(12) United States Patent
Johnson et al.

(10) Patent No.: US 8,845,566 B2
(45) Date of Patent: Sep. 30, 2014

(54) ACTIVE EXOSKELETAL SPINAL ORTHOSIS AND METHOD OF ORTHOTIC TREATMENT

(71) Applicant: The Regents of the University of Michigan, Ann Arbor, MI (US)

(72) Inventors: Daniel D. Johnson, Ann Arbor, MI (US); James A. Ashton-Miller, Ann Arbor, MI (US); Albert J. Shih, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 0 days.

(21) Appl. No.: 13/957,092

(22) Filed: Aug. 1, 2013

(65) Prior Publication Data

US 2014/0039371 A1 Feb. 6, 2014

Related U.S. Application Data

(60) Provisional application No. 61/678,773, filed on Aug. 2, 2012.

(51) Int. Cl.
*A61F 5/00* (2006.01)
(52) U.S. Cl.
USPC .............................................. 602/16; 602/19
(58) Field of Classification Search
USPC ......... 602/5, 16, 20–28; 128/882; 5/621, 624; 601/35, 84
See application file for complete search history.

(56) References Cited

U.S. PATENT DOCUMENTS

| | | | |
|---|---|---|---|
| 5,020,790 A | 6/1991 | Beard et al. | |
| 5,252,102 A | 10/1993 | Singer et al. | |
| 6,743,187 B2 | 6/2004 | Solomon et al. | |
| 6,966,882 B2 | 11/2005 | Horst | |
| 7,190,141 B1 | 3/2007 | Ashrafiuon et al. | |
| 7,204,814 B2 | 4/2007 | Peles | |
| 7,416,537 B1 | 8/2008 | Stark et al. | |
| 7,731,670 B2 | 6/2010 | Aguirre-Ollinger et al. | |
| 7,774,177 B2 | 8/2010 | Dariush | |
| 8,066,654 B2 | 11/2011 | Sandifer et al. | |
| 8,083,694 B2 | 12/2011 | Peles | |
| 8,235,924 B2 * | 8/2012 | Bachmann et al. | 602/16 |
| 2003/0030397 A1 * | 2/2003 | Simmons | 318/568.11 |
| 2007/0123997 A1 * | 5/2007 | Herr et al. | 623/27 |
| 2010/0094188 A1 * | 4/2010 | Goffer et al. | 602/23 |
| 2011/0040216 A1 * | 2/2011 | Herr et al. | 601/34 |
| 2011/0166491 A1 * | 7/2011 | Sankai | 601/84 |

OTHER PUBLICATIONS

H.J. Wilke, P. Neef, M. Caimi, T. Hoogland, L.E. Claes, "New In Vivo Measurements of Pressures in the Intervertebral Disc in Daily Life," SPINE 24(8), 1999, pp. 755-762.

(Continued)

*Primary Examiner* — Michael A. Brown
(74) *Attorney, Agent, or Firm* — Reising Ethington P.C.

(57) ABSTRACT

An active exoskeletal spinal orthosis that can reduce the spinal compression and muscle effort involved in resisting gravitational bending moments. The spinal orthosis includes upper and lower members that fit around the body in the area of the spine. Actuators extend between the upper and lower members. By applying a corrective moment, a distraction force, or both to a user via the actuators, the spinal orthosis allows for supported multi-planar maneuverability within a set range of motion. A controller activates the actuators based on sensor feedback that is indicative of pressure or some other sensed physical parameter related to the bending moment.

12 Claims, 6 Drawing Sheets

(56) References Cited

OTHER PUBLICATIONS

M.A. Adams, D.W. McMillan, T.P. Green, P. Dolan, "Sustained Loading Generates Stress Concentrations in Lumbar Intervertebral Discs," SPINE 21(4), 1996, pp. 434-438.

R. Ortengren, G.B.J. Andersson, A.L. Nachemson, "Studies of Relationships Between Lumbar Disc Pressure, Myoelectric Back Muscle Activity, and Intra-Abdominal (Intragastric) Pressure," SPINE 6(1), 1981, pp. 98-103.

P.F. Flanagan, T.M. Gavin, D.Q. Gavin, A.G. Patwardhan, "Spinal Orthoses," Chapter 14, in Lusardi and Nielson Eds. Orthotics and Prosthetics in Rehabilitation, Butterworth-Heinemann Publishers, Newton Massachusetts, Jun. 2000, pp. 231-252.

M. Bussel, J. Merritt, L. Fenwick, "Spinal Orthoses," Chapter 4, in Redford, Basmajian, and Trautman Eds. Orthotics: Clinical Practice and Rehabilitation Technology, 1st Edition, Churchill Livingstone, Philadelphia, PA, Sep. 8, 1995, pp. 71-101.

J. Cholewicki, N.P. Reeves, V.Q. Everding, D.C. Morrisette, "Lumbosacral Orthoses Reduce Trunk Muscle Activity in a Postural Control Task," Journal of Biomechanics 40, Elsevier, Durham, NC, 2007, pp. 1731-1736.

J.T. Wassell, L.I. Gardner, D.P. Landsittel, J.J. Johnston, J.M. Johnston, "A Prospective Study of Back Belts for Prevention of Back Pain and Injury," JAMA 284(21), Dec. 6, 2000, pp. 2780-2781.

G.P. Bernardoni and T.M. Gavin, "Comparison Between Custom and Noncustom Spinal Orthoses," Phys. Med. Rehabil. Olin. N. Am. 17, 2006, Elsvier Saunders, Durham, NC, pp. 73-89.

S.A. Lantz and A.B. Schultz, "Lumbar Spine Orthosis Wearing I. Restriction of Gross Body Motions," SPINE 11(8), 1986, pp. 834-837.

S.A. Lantz and A.B. Schultz, "Lumbar Spine Orthosis Wearing II. Effect on Trunk Muscle Myoelectric Activity," SPINE 11(8), 1986, pp. 838-842.

H. Perner-Wilson, L. Buechley, M. Satomi, "Handcrafting Textile Interfaces from a Kit-of-No-Parts," TEI '11 Proceedings of the Fifth International Conference on Tangible, Embedded, and Embodied Interaction, 2011, ACM, New York, NY, pp. 61-68.

\* cited by examiner

ACTIVE EXOSKELETAL SPINAL ORTHOSIS AND METHOD OF ORTHOTIC TREATMENT

CROSS-REFERENCE TO RELATED APPLICATION

This application claims the benefit of U.S. Provisional Ser. No. 61/678,773 filed on Aug. 2, 2012, the entire contents of which are hereby incorporated by reference.

TECHNICAL FIELD

This invention relates to spinal orthotics and methods of spinal orthotic treatment.

BACKGROUND

The biomechanical mechanisms underlying spinal flexion and extension are unique in comparison with other appendages. The spine is primarily loaded in compression, the magnitude of which can be measured invasively via the internal pressure developed in the nucleus pulposus of the intervertebral discs. The nucleus pulposus at the core of each disc and the surrounding annulus fibrosis together act as a hydraulic cushion that provides uniform hydrostatic force to separate each vertebrae of the spine. The thickness and pressure within each disc are largely dependent on the amount of fluid contained in the intervertebral disc, which can decrease by as much as 20% over the course of a day of normal activity in healthy people. The magnitude of the pressure developed in the intervertebral disc is directly related to the degree of postural back muscle activation.

Spinal orthoses are often prescribed to lessen the degree of postural back muscle activation by restricting the motion of the spine and/or offloading the spinal column following spinal surgery or trauma. Spinal offloading is typically achieved through one of two mechanisms. First, the application of three-point bending to the trunk in the sagittal plane can reduce spinal loading. An example is the Jewett hyperextension orthosis (Florida Brace Corp., Orlando, Fla.), which applies two posteriorly-directed forces at the thorax and pelvis and one anteriorly directed force at the lumbodorsal region of the trunk, offloading the anterior thoracolumbar vertebral bodies to promote the healing of compression fractures. Although this type of orthosis allows for a range of motion, little or no support is provided until the wearer reaches the limits of the range of motion, where the structure of the orthosis comes into sustained contact with the wearer and support is applied.

Second, increasing intraabdominal cavity pressure can reduce spinal loading. Lumbosacral orthoses, such as soft belts and semi-rigid corsets, can reduce the muscle effort required to maintain a stable neutral posture. Soft belts and semi-rigid corsets are the most commonly used forms of spinal orthoses used outside of a clinical setting, and they are typically used with the intention of preventing or treating lower back pain of workers performing occupations with frequent bending and lifting. Despite the common use of such orthoses, the use of such commercially-available back belts does not provide a reduction in the likelihood of injury. Custom-made orthoses produced by a trained orthotist have been shown to be more biomechanically effective than common off-the-shelf models, but have several predominant drawbacks. First, the individual manufacturing and fitting required are prohibitively expensive for common usage. Second, the restricted maneuverability such orthoses create could be disadvantageous in the workplace. Lastly, some custom-made corset-style orthoses can result in increased back postural muscle activity that could promote muscle fatigue.

Spinal orthoses in general reduce the effort required of the postural muscles and also the compressive load they add to the spine. This is accomplished when an orthosis produces its own corrective moment, created from normal contact stress applied to the skin of the user. However, as mentioned above, current orthosis designs that allow for a range of motion provide little or no support until the wearer reaches the limits of the range of motion. At this point, the structure of the orthosis comes into sustained contact with the wearer and support is applied. Thus, there is a gap in support when maneuverability is allowed. For the foregoing reasons, there is a need for a non-custom orthosis which would reduce spinal compression and muscle effort in resisting gravitational bending moments due to the mass of the trunk, while simultaneously allowing multi-planar maneuverability within a set range of motion.

SUMMARY

According to one embodiment, there is provided an active exoskeletal spinal orthosis, including an upper member and a lower member that can extend circumferentially around a user and can be attached to the user at two spaced locations that are separated by at least a portion of the user's spine. The active exoskeletal spinal orthosis includes a plurality of actuators that extend between the upper and lower member and at least one sensor measuring one or more physical parameters indicative of a bending moment caused by gravity, a bending moment caused by muscle force, or a bending moment caused by both gravity and muscle force. The active exoskeletal spinal orthosis further includes a controller that receives input from the sensor(s) and activates one or more of the actuators to apply a corrective moment, a distraction force, or both, which at least partially counteracts the bending moment applied by the user.

According to another embodiment, there is provided a method of orthotic treatment, including the steps of attaching an orthosis to a user at two spaced locations along portions of the user's torso, detecting a bending of the spine by the user when pressure is applied to at least a part of the orthosis, and applying a corrective moment, a distraction force, or both to the user's spine. The corrective moment, the distraction force, or both at least partially counteract the detected bending of the spine by actuating one or more of a plurality of actuators that extend between an upper member and a lower member of the orthosis.

BRIEF DESCRIPTION OF THE DRAWINGS

Preferred exemplary embodiments will hereinafter be described in conjunction with the appended drawings, wherein like designations denote like elements, and wherein.

DETAILED DESCRIPTION OF THE ILLUSTRATED EMBODIMENTS

The description below is directed to a method of orthotic treatment using an active exoskeletal spinal orthosis that is suitable for use outside of a clinical setting and can provide a user's spine with support throughout a range of motion.

Figure 1A:
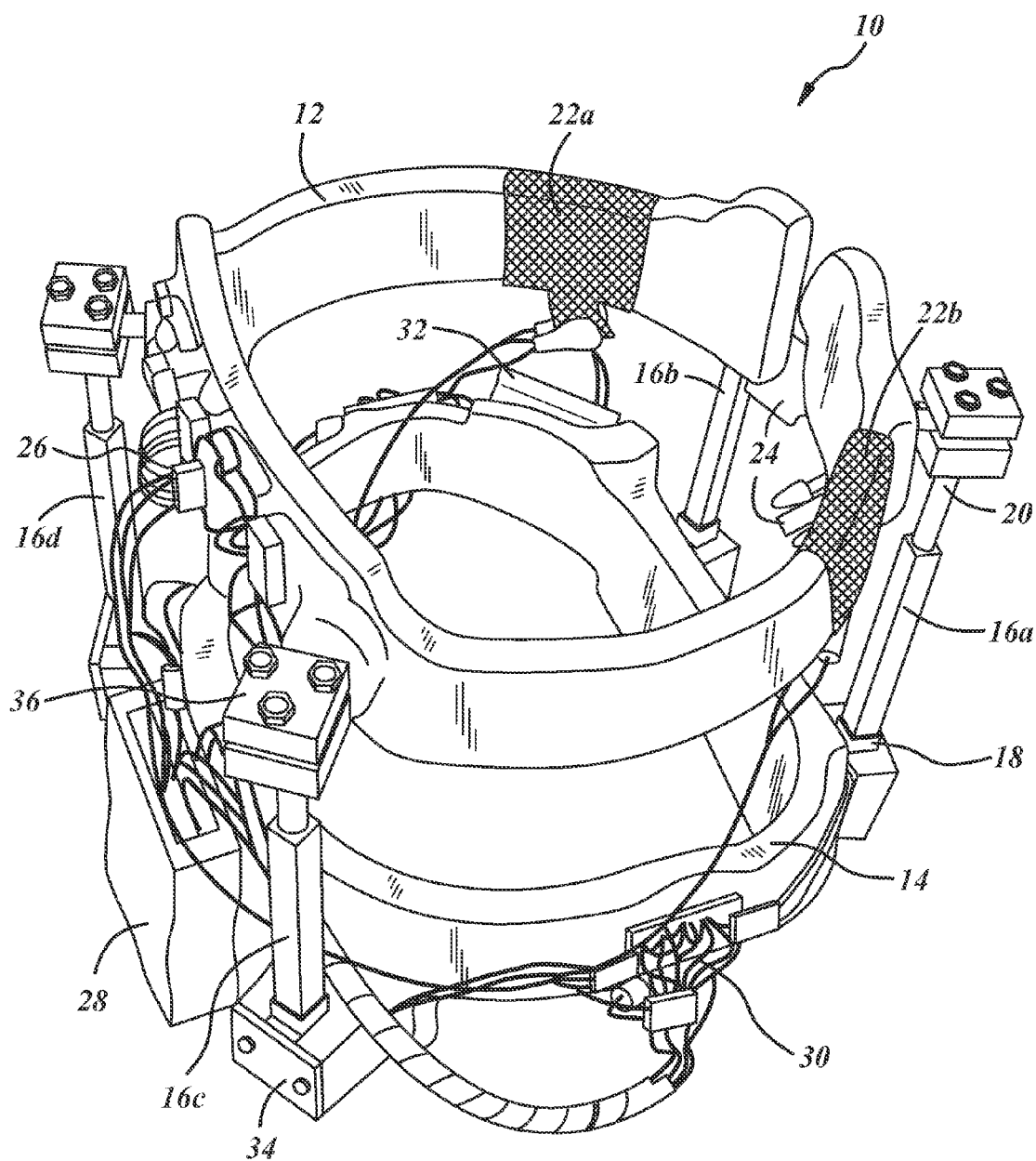
FIG. 1A shows an isometric view of an active exoskeletal spinal orthosis, according to one embodiment.
Figure 1B:
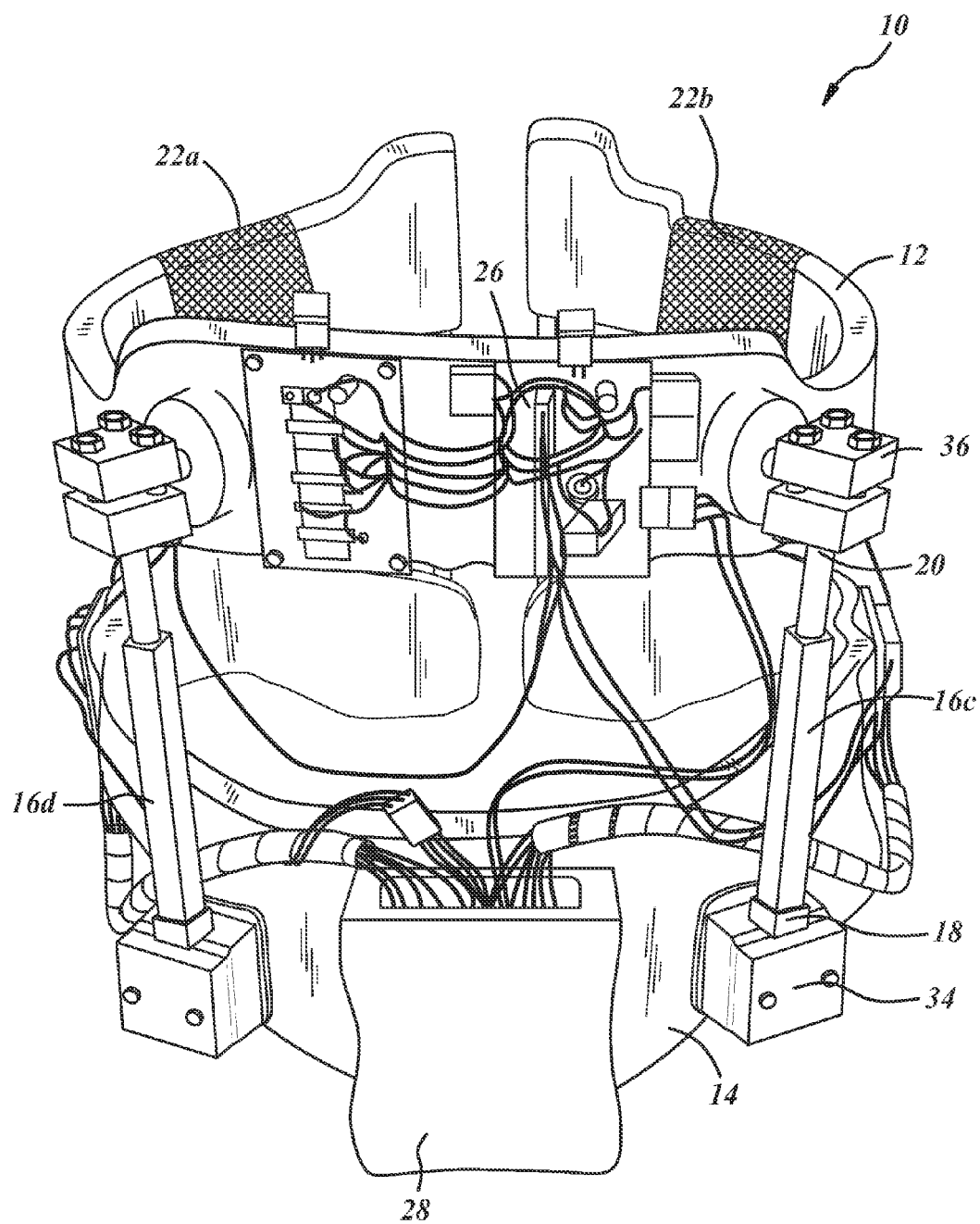
FIG. 1B shows a posterior view of the active exoskeletal spinal orthosis of FIG. 1A.

As shown in FIG. 1A and FIG. 1B, an illustrative active exoskeletal spinal orthosis 10 comprises an upper member 12, a lower member 14, and a plurality of actuators 16a, 16b, 16c, 16d. Each actuator 16 has a first end 18 and a second end 20. The first end 18 is coupled to the lower member 14, and the second end 20 is coupled to the upper member 12 such that the actuators 16a, 16b, 16c, 16d extend between the lower member 14 and the upper member 12. In the illustrated embodiment, two sensors 22a, 22b are disposed on the inner surface of the upper member 12. A sensor circuit 26 comprises a combination driver/filter/amplifier circuit that is situated on the posterior portion of the outer surface of the upper member 12. An adjustable strap and buckle 24 is attached at each end of the outer surface of the upper member 12, allowing the user to tighten the orthosis. A controller 28 can be disposed on the outer surface of the lower member 14. Controller 28 receives the sensor data from circuit 26 and generates output actuator drive signals that activate the actuators 16. Controller 28 may include a processor, computer-readable memory, and a communication circuit. A motor driver circuit 30 is situated on the lower member 14 between anterior actuator 16a and posterior actuator 16c. Another motor driver circuit (not shown) is situated on the lower member 14 between anterior actuator 16b and posterior actuator 16d. These motor drive circuits receive the output actuator signals from controller 28 and provide suitable drive power for the individual actuators 16. The construction and operation of suitable motor drive circuits will be apparent to those skilled in the art.

Additionally, a method is disclosed for a form of spinal orthotic treatment whereby the allowed range of motion and perceived mechanical response of the orthosis within that range of motion can be arbitrarily chosen and adjusted via reprogramming of the control system of the orthosis. The orthosis, which can be, for example, orthosis 10, produces this behavior by means of a closed-loop control system utilizing one or more types of sensors that monitor the physical state at the orthosis/skin interface and an actuation system that can reconfigure the shape of the orthosis to maintain that physical state within permissible values.

The sensors 22a, 22b measure one or more physical parameters indicative of a bending moment being applied by the user due to gravity and/or muscle forces to the orthosis. The controller 28 receives input from the sensors 22a, 22b via circuit 26 and activates one or more of the actuators 16a, 16b, 16c, 16d via the motor driver circuits 30 to apply a corrective moment and/or a distraction force to the user's spine that at least partially counteracts the bending moment applied by the user. Application of a corrective moment involves use of the actuators to at least partially counteract a sensed bending moment being applied by the user. In contrast to a corrective moment, the distraction force is a generally upward force pushing parts of the spine apart, which can counteract the weight of the thorax. The corrective moment and/or distraction force can be applied continuously throughout a range of motion. As an example, the controller 28 can be set to induce flexion through in the orthosis by having the anterior actuators 16a, 16b retract while the posterior actuators 16c, 16d extend when the sensor signals exceed a maximum threshold, thereby applying a corrective moment. If the sensor signals remain within a set range of permissible values or the actuators 16c, 16d reach maximum extension, the orthosis will be held at that current level of flexion. If the sensor signals drop below a minimum threshold, the controller 28 will induce extension in the orthosis by extending the anterior actuators 16a, 16b and retracting the posterior actuators 16c, 16d until the sensor signals are within the chosen threshold, at which point the controller 28 will stop the actuators 16. The actuators 16 may also include a sensor that allows the controller 28 to monitor the position of the orthosis relative to the pelvis and/or the position of the orthosis relative to the adjustable endpoints or mechanical limits of the actuators. The orthosis 10 may move with its user until encountering the programmed threshold or the limits of the actuators 16. The orthosis is not limited to flexion and extension within the sagittal plane. Motion can be possible in all three body planes. For example, using various types and numbers of actuators, it could be possible to achieve flexion and extension in the sagittal plane, lateral bending in the coronal plane, and axial rotation in the transverse plane. During such motion, the orthosis is capable of applying a nonlinear or variable corrective moment and/or distraction force as needed. As further described below, the exact level of support of the orthosis can be adjusted by the user or a clinician without requiring any structural changes to the orthosis.

With reference to FIG. 1A and FIG. 1B, the controller 28 may include a processor, computer-readable memory, and a communication circuit, capable of storing one or more programs that can be executed by the processor to record data concerning operation of the orthosis and communicate the data externally from the orthosis. This addition of communication and logging capabilities would be particularly beneficial in a clinical setting. At their own convenience, clinicians would be able to remotely monitor the state of treatment, including but not limited to the level of applied support, patient compliance, and activity levels. Furthermore, this system would allow a clinician to adjust the behavior of the orthosis remotely, thereby reducing the number of required in-person visits for orthosis adjustment and monitoring.

Figure 3:
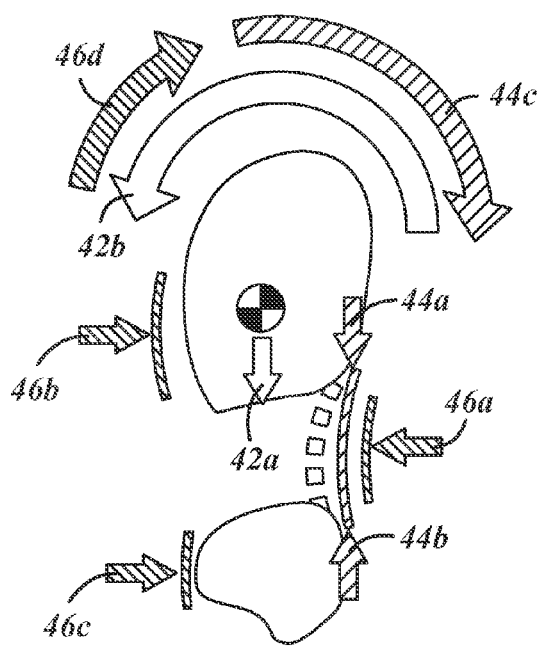
FIG. 3 is a free-body diagram of forces acting on the trunk.
Figure 4:
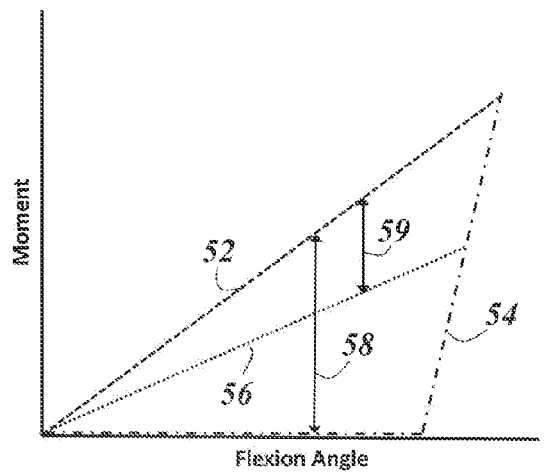
FIG. 4 is a graphical depiction of typical moment vs. flexion angle relationships for a body-orthosis system.

FIG. 3 and FIG. 4 together demonstrate the underlying biomechanical function of the proposed active exoskeletal spinal orthosis compared with a traditional passive spinal orthosis that allows for a range of motion. The spine is primarily loaded in compression. However, in order for the trunk to remain stationary, the postural muscles of the lower back must contract with sufficient force to produce a corrective moment 44a, 44b which can counteract the moment produced by gravity 42a as shown in the free-body diagram of forces acting on the trunk in FIG. 3. Traditional passive spinal orthoses can reduce the effort required of the postural muscles, thereby reducing the compressive load they add to the spine. This is accomplished when a traditional passive spinal orthosis produces its own corrective moment 46, created from normal contact stress applied to the skin of the wearer. The traditional passive spinal orthosis applies one anteriorly-directed force 46a at the lumbodorsal region of the trunk and two posteriorly-directed forces at the thorax 46b and pelvis 46c, offloading the anterior thoracolumbar vertebral bodies. It should be noted that FIG. 3 diagrams only one example of moment generation by a traditional orthosis, as it is possible to hold a user in flexion with two anteriorly-directed forces and one posteriorly-directed force as well. Although this traditional type of orthosis allows for a range of motion, little or no support is provided until the wearer reaches the limits of the range of motion, where the structure of the orthosis comes into sustained contact with the wearer and support is applied. Accordingly, there is a decrease or gap in support at any point where the body is allowed to move away from the orthosis.

FIG. 4 is a graphical depiction of the typical moment vs. flexion angle relationships for a body-orthosis system. The gravitational moment 52 must be exactly counterbalanced by the corrective moments produced by the postural muscles 58, 59 and the corrective moments produced by an orthosis 54, 56, if present. Thus, the corrective moments produced by the postural muscles 58, 59 and the corrective moments produced by an orthosis 54, 56 must sum to counterbalance the gravitational moment 52. The muscular corrective moment 58 corresponding to use with a traditional passive spinal orthosis that allows for a range of motion is larger because of the gap in support that occurs until the structure of the orthosis comes into sustained contact with the wearer and support is applied. During this gap in support, the postural muscles must provide all of the corrective moment 58 to counteract gravity. Accordingly, a larger muscle corrective moment 58 is required. An active exoskeletal spinal orthosis corrective moment 56, on the other hand, provides support throughout a range of motion, and would thus require a smaller muscular corrective moment 59 and decreased muscle effort compared with the traditional passive orthosis. The inclusion of a control system which reacts to the observed spinal moments and alters the magnitude and distribution of the moments to match desired specifications allows for the smaller muscular corrective moment 59. Applying a corrective moment to the thorax via a corrective support applied anteriorly to the spine, as the orthosis embodiment shown in FIG. 1 and FIG. 2 does, can reduce the corrective moment 59 required of the lower back muscles in order to balance the gravitational flexion moments 52 of the thorax. Such a reduction in the corrective moment 59 results in a corresponding reduction in muscle force and activity.

In the illustrated embodiment of spinal orthosis 10 as shown in FIG. 1A and FIG. 1B, upper member 12 may be a plastic segment that extends circumferentially around the thorax of the user. Upper member 12 could also encircle the user. In the illustrated embodiment, the buckle and adjustable-length strap 24, which allows the upper member 12 to be tightened around the thorax, is attached to the anterior of the upper member 12 with two Chicago-style screws (not shown) embedded in the upper member 12. Lower member 14 may be a plastic segment that extends circumferentially around the pelvis, making contact at the sacrum and iliac crests. In this particular embodiment, upper member 12 and lower member 14 are InstaMorph semi-flexible plastic segments (Happy Wire Dog, LLC, Scottsdale, Ariz.), although other materials may be used for the upper member 12 and lower member 12 so long as there is a sufficient rigidity to withstand the requisite forces.

Figure 2:
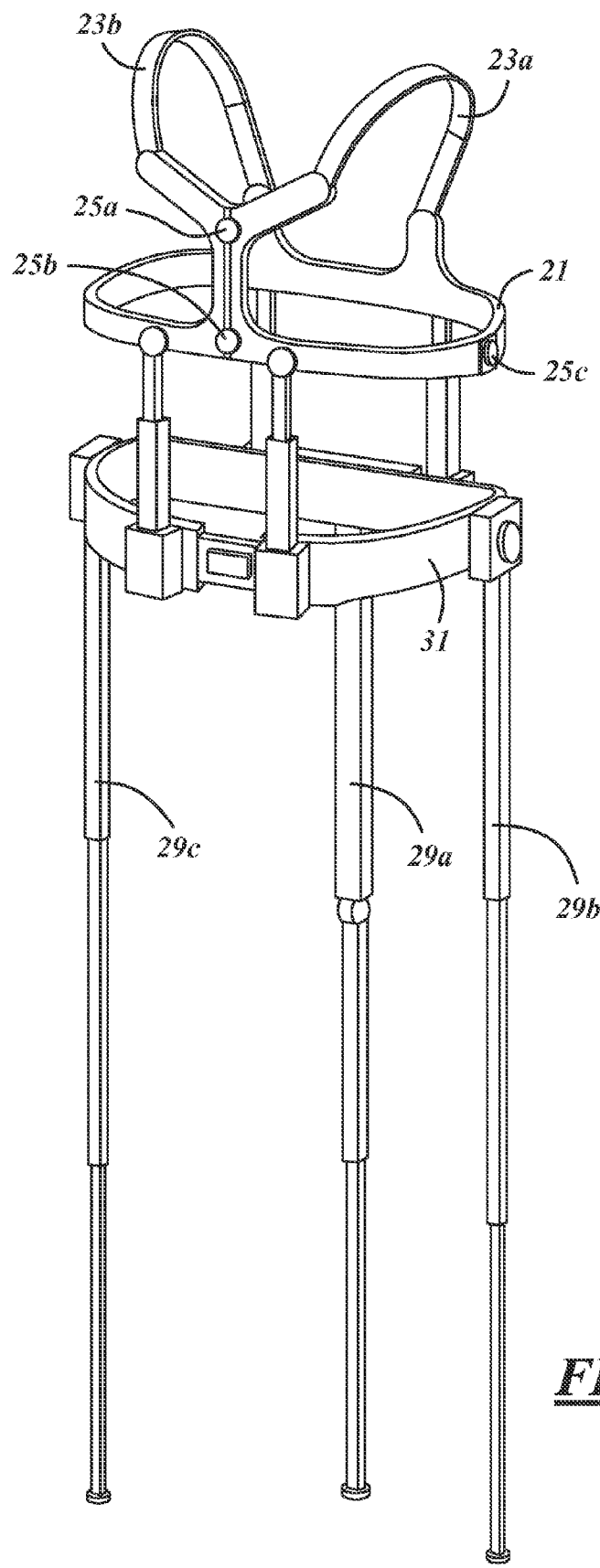
FIG. 2 shows a front, isometric view of an active exoskeletal spinal orthosis, according to one embodiment.

FIG. 2 shows another embodiment of the active exoskeletal spinal orthosis with a structurally distinct upper member 21. This particular embodiment has shoulder straps 23a, 23b which extend from the upper member 21. The shoulder straps 23a, 23b can be attached to the upper member 21 or to any operable location on the orthosis. Alternatively, the shoulder straps 23a, 23b could be a uniform part of the upper member 21. The shoulder straps 23a, 23b can be rigid or semi-rigid and may be adjustable. Furthermore, the shoulder straps 23a, 23b may be load-bearing. As an example, surgeons who must hold an erect posture for a prolonged period of time while wearing a lead vest could wear the vest over the shoulder straps 23a, 23b. The weight of the vest could be borne by the shoulder straps 23a, 23b to the rest of the orthosis, thus ensuring that the lead vest does not weigh down the surgeon's neck and shoulders. Fasteners 25a, 25b are coupled to upper member 21 such that the orthosis circles the user around the ribcage. Segments of the upper member 21 could be coupled with any adequate form of closure, for example with a locking detent mechanism or zipper. Upper member 21 and lower member 31 may also have hinges at the midline, allowing the user to open the orthosis.

The embodiment illustrated in FIG. 2 also shows a structurally distinct lower member 31, that can include a leg member 29 that could extend to the floor. The leg member 29 could also take the form of a seat. The pictured embodiment shows three leg members 29a, 29b, 29c. However, it is possible to use one or more leg members. The leg member could be coupled with the orthosis itself, for example with hinges, brackets or a clutch mechanism, or could be separate from the orthosis. Furthermore, the leg members 29a, 29b, 29c could be coupled to the orthosis in any sufficiently operable location, such as to upper member 21. The user could store the leg members 29a, 29b, 29c in a refracted position with the orthosis. The leg members 29a, 29b, 29c could be retracted using any suitable method, such as telescopic extension. Leg members 29a, 29b, 29c could be deployed telescopically so as to be in contact with a support surface, such as the ground, via a high-friction tip or suction cup, for example, and locked in position at a desired length and angle. Each leg member 29 in the illustrated embodiment has the rigidity to support both bending and compressive loads.

With reference to the embodiment illustrated in FIG. 1A and FIG. 1B, yet applicable to any particular embodiment, the actuators 16a, 16b, 16c, 16d are linear actuators (L12-100-210-06-P; Firgelli Technologies, Inc., Victoria, BC, CAN). Although the illustrated embodiment shows four actuators, similar functionality can be achieved with two or more actuators. The anterior actuators 16a, 16b and posterior actuators 16c, 16d are coupled to upper member 12 and lower member 14 such that each is approximately 30° from the respective midline. The first end 18 of each actuator 16 can be rigidly mounted to the lower member 14 with aluminum brackets 34, although other suitable mounting means will be apparent to one having ordinary skill in the art. The second end 20 of each actuator 16 is coupled to the upper member 12 with a ball-and-socket joint, the socket 36 of which is attached to the second end 20 of the actuator 16. The ball can be fabricated from nylon and attached to the upper member 12. The sockets 36 in this embodiment are comprised of two Delrin pieces (DuPont, Wilmington, Del.) held together with three nut-and-bolt assemblies. By tightening or loosening the nuts on each socket 36, the friction created with the ball can be increased or decreased, respectively. In this embodiment, the actuators 16 have their speed and direction controlled by two motor driver circuits (TB6612FNG; Toshiba Corp., Tokyo, JPN) that are repackaged on secondary circuit boards for through-hole wiring (ROB-09457; SparkFun Electronics, Boulder, Colo.). In FIG. 1A, one motor driver unit 30 is shown disposed on the outer surface of the lower member 14 at the midline between the anterior actuator 16a and the posterior actuator 16c. The other motor driver unit is not shown, but it may be disposed on the outer surface of the lower member 14 at the midline between the anterior actuator 16b and posterior actuator 16d. The motor driver units 30 and the actuators 16 are powered by a single 4×AA-type battery pack 32 attached to lower member 14 adjacent to the anterior actuator 16b, although other means of powering the motor driver units will be apparent to one having ordinary skill in the art.

With reference to the illustrated embodiment of FIG. 1A and FIG. 1B, two sensors 22a, 22b monitor the corrective flexion-extension moment being applied to the user of the orthosis. In this particular embodiment, sensors 22a, 22b are conductive-fabric piezoresistive sensors, a type of force sensitive resistance (FSR) sensor. Each sensor 22 has an active sensing area of approximately 3.5 cm×5.5 cm, and is secured to the inner surface of the upper member 12 by using adhesive tape, for example. The leads connecting each sensor 22 to the rest of the control system are detachable and long enough to allow for each sensor 22 to be repositioned anywhere on the perimeter of the upper member 12. The sensors 22a, 22b may be placed in any operable location on the orthosis.

Figure 5:
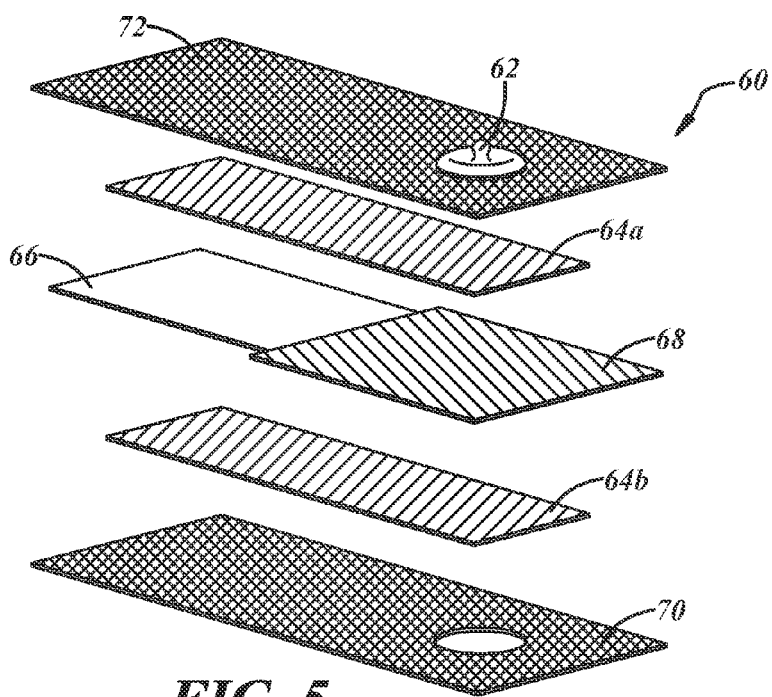
FIG. 5 shows an exemplary piezoresistive contact stress sensor.
Figure 6:
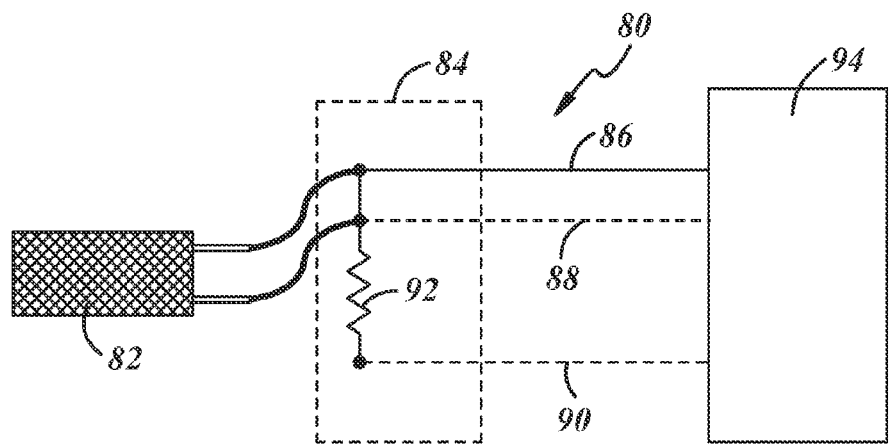
FIG. 6 is a sensor circuit, according to one embodiment.
Figure 7:
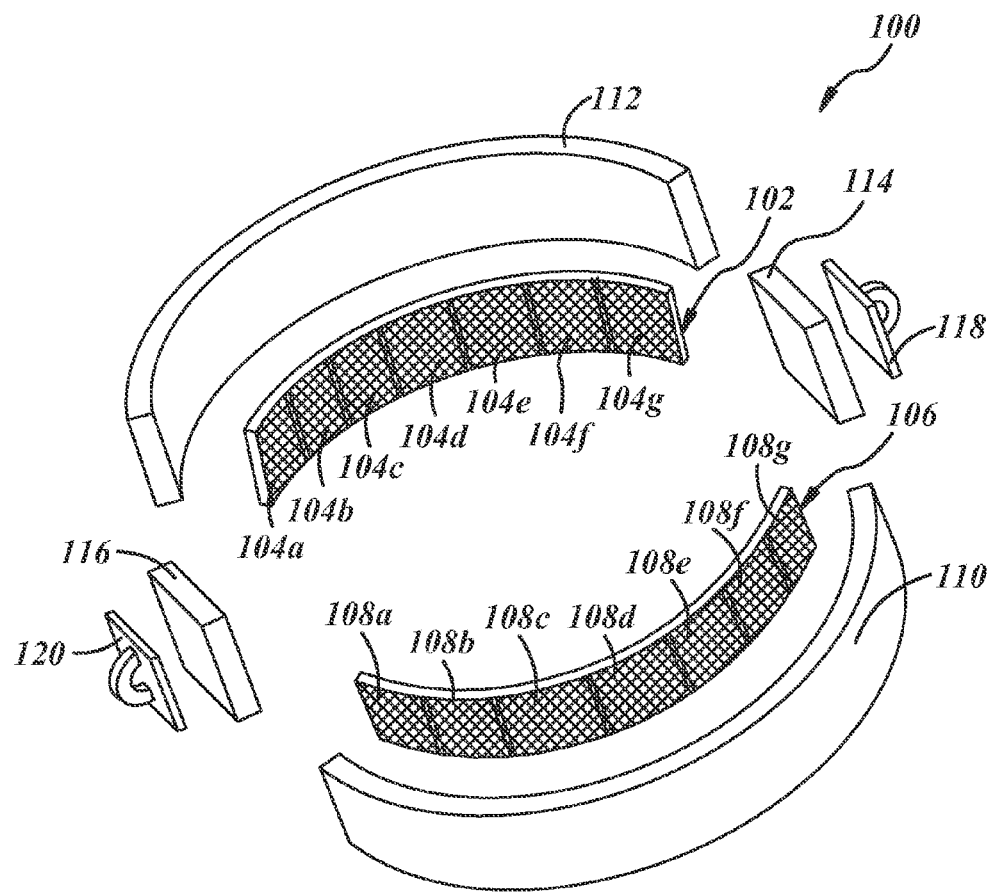
FIG. 7 shows an embodiment of an upper member of a spinal orthosis with accompanying sensors.

FIG. 5 shows another embodiment of a piezoresistive contact stress sensor 60. A polyester separator layer 68 and conductive fabric layer 66 (ArgenMesh; Less EMF Inc., Latham, N.Y.) are situated between two layers of conductive film 64a, 64b (Velostat; 3M, St. Paul, Minn.). A polyester outer shell layer 70, is situated next to conductive film layer 64b and makes contact with the user of the orthosis. A polyester inner shell layer 72 is situated on the conductive film layer 64a. A snap fastener 62 can serve to attach the assembled sensor 60 to the orthosis. The sensor layers 62, 64, 66, 68, 70, 72 are assembled together, for example by sewing or gluing. FIG. 6 shows an example electronic schematic 80. The electrical resistance of the sensor 82 decreases as increased contact stress is applied to the active sensor area. An alternative embodiment of an upper member of an orthosis is shown in FIG. 7. Unlike the embodiment illustrated in FIG. 1A and FIG. 1B, the upper member 100 is comprised of two lateral segments 110, 112, a posterior segment 114, and an anterior segment 116, which can all be comprised of a flexible plastic or other suitable material. Lateral segments 110, 112 can extend circumferentially around the user's ribcage. Posterior segment 114 and anterior segment 116 are flat padded plates with posterior line attachment point 118 and anterior line attachment point 120 for sensor leads or other cabling. Posterior segment 114 is situated over the spine of the user, and anterior segment 116 is situated over the sternum of the user. Lateral segments 110, 112, posterior segment 114, and anterior segment 116 are assembled together, for example with nylon webbing and buckles, which allow separation between the segments to be adjusted. Lining the inner surface of lateral segment 112 is sensor array 102. Sensor array 102 is comprised of seven sensors 104a-g. Lining the inner surface of lateral segment 110 is sensor array 106, which is also comprised of seven sensors 108a-g. Referring to the electrical schematic in FIG. 6, in order to measure the change in resistance, each sensor 82, as well as sensors 104a-g, 108a-g in FIG. 7 may be placed in series with a 10 kΩ resistor 92 as part of a voltage divider circuit 84. Each sensor array 102, 106, with reference to FIG. 6 and FIG. 7, share a single driving voltage input 86 of +5V DC and a single local ground 90. The circuit signal 88 of each sensor 82 is sampled by an analog input channel at 1 kHz via a 16-bit DAQCard-6024E (National Instruments, Inc., Austin, Tex.) 94 analog-to-digital converter board and notebook PC running LabVIEW version 9.0 (National Instruments, Inc., Austin, Tex.) (not shown). In another embodiment, a plurality of sensors can extend around the entire inner perimeter of the upper member 12 such that the controller can construct a pressure map of where and how much force the user is applying to the orthosis.

Although the illustrated embodiment of the orthosis uses piezoresistive sensors to measure contact stress, a number of other types of sensors could be used or other physical parameters could be measured instead of, or in addition to stress or strain. For example, sensors could be used to measure one or more of the following types of physical parameters: stress, strain, temperature, humidity, position, velocity, acceleration, orientation, or muscle activity. Similarly, there can be variations as to the construction and relative functionality of the sensors themselves. For example, instead of the piezoresistive contact stress sensor 82 shown in FIG. 6, a fluid bladder sensor could be used to monitor stress or strain.

Figure 8:
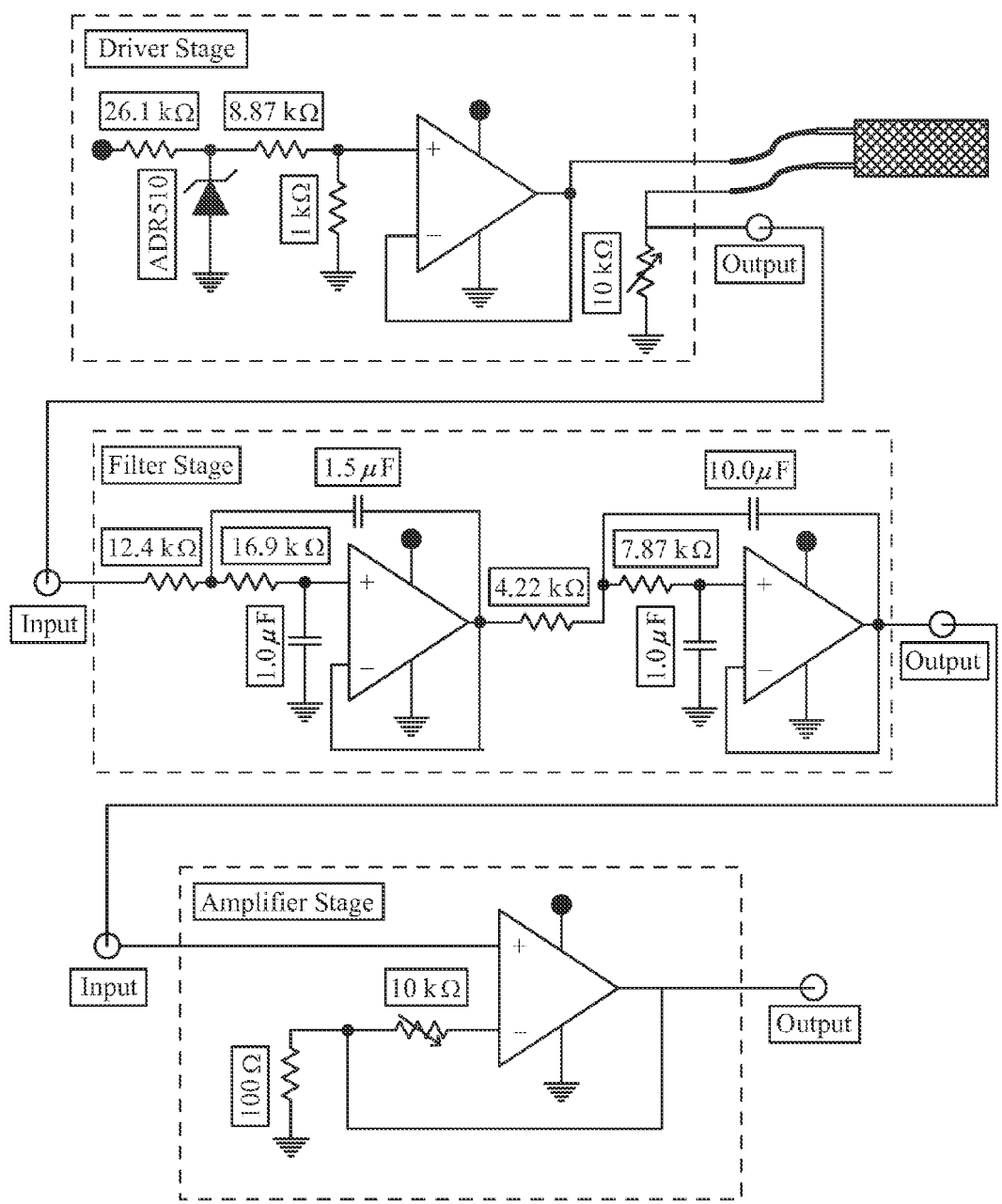
FIG. 8 is a sensor circuit, according to one embodiment.

With reference to the particular embodiment illustrated in FIG. 1A and FIG. 1B, the controller 28 may be a microcontroller (Arduino Nano v3; Gravitech, Claremont, Calif.) that may not be capable of measuring resistance levels from each piezoresistive sensor 22a, 22b directly. In such a circumstance, the resistance value from each sensor 22a, 22b may be converted into an analog voltage by means of the sensor circuit 26, which is represented in detail in FIG. 8. In the illustrated embodiment, the sensor circuit 26 is situated on two circuit boards mounted to the posterior of the upper member 12. The active components of the circuit used in the particular embodiment are 12 operational amplifiers (LM4091-2; Analog Devices, Inc., Norwood, Mass.), two voltage regulators (LF90CV; STMicroelectronics, Geneva, CHE), and one voltage reference (ADR510; Analog Devices, Inc., Norwood, Mass.). As shown in FIG. 8, the driver portion may be structured to place each sensor in a voltage divider. 100 mV is applied to each sensor, which is then in series with a 10 kΩ linear potentiometer that is set to approximately match the resistance of its associated sensor when under load. The sensor signal, which is affected by ambient electrical noise, next passes through the filter portion of the circuit. In this particular embodiment, the filter is a fourth-order Butterworth type, arranged in a Sallen-Key topology, with the corner frequency fc (−3 dB attenuation) set to 10 Hz and the stop frequency fs (−30 dB) set to 60 Hz. To take advantage of the full measurement resolution of the controller 28 of the control system in this embodiment, the filtered signal next passes through a non-inverting amplifier with a tunable gain, which is adjusted such that the maximum value of the sensor signal is approximately 5V, the maximum value that can be measured by the controller 28 in the illustrated embodiment. The sensor circuit 26 and controller 28 are powered in this particular embodiment by a single 9V battery contained within the controller 28. Position feedback is provided from each actuator 16 to the controller 28 by an internal potentiometer which, in this embodiment, outputs an analog voltage that varies linearly between 0V and 5V, depending on the length the actuator 16 is extended relative to its full stroke length. Other types of feedback may be included in addition to or instead of using a potentiometer, such as using an accelerometer or motion detector, for example. In an embodiment with logging and communication capabilities, such feedback could be recorded and used for treatment purposes by the user or clinician, for example. The programming used by the controller 28 to determine and apply the derived corrective moment and/or distraction force can include whatever algorithm is suitable to achieve the desired response. This can be determined empirically or otherwise, and is within the level of skill in the art.

It is to be understood that the foregoing description is of one or more preferred exemplary embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "for example," "e.g.," "for instance," and "such as," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

The invention claimed is:

1. An active exoskeletal spinal orthosis, comprising:
    an upper member comprising one or more upper body portions that together can extend circumferentially around a body part of a user;
    a lower member comprising one or more lower body portions that together can extend circumferentially around the user at a location below the upper member, wherein the upper and lower members can be attached to the user at two spaced locations that are separated by at least a portion of the user's spine;
    a plurality of actuators, each actuator having a first end and a second end;
    wherein the first end of each actuator is coupled to the lower member and the second end of each actuator is coupled to the upper member such that the actuators extend between the lower member and the upper member;
    at least one sensor measuring one or more physical parameters indicative of a bending moment caused by gravity, a bending moment caused by muscle force, or a bending moment caused by gravity and muscle force; and
    a controller that receives input from the sensor(s) and activates one or more of the actuators to apply a corrective moment, a distraction force, or both to the user's spine that at least partially counteracts the bending moment applied by the user.

2. The active exoskeletal spinal orthosis of claim 1, wherein the controller activates one or more of the actuators in response to the sensor input to provide a corrective moment, a distraction force, or both that is continuous throughout a range of motion.

3. The active exoskeletal spinal orthosis of claim 1, wherein the controller includes a processor, computer-readable memory, and a communication circuit, the computer readable memory storing one or more programs that can be executed by the processor to record data concerning operation of the orthosis and communicate the data externally from the orthosis.

4. The active exoskeletal spinal orthosis of claim 1, wherein the sensors measure one or more of the following types of physical parameters: stress, strain, temperature, humidity, position, velocity, acceleration, orientation, or muscle activity.

5. The active exoskeletal spinal orthosis of claim 1, wherein the upper member is configured to attach to the user at an upper torso part of the user and the lower member is configured to attach to the user at a lower torso part of the user.

6. The active exoskeletal spinal orthosis of claim 1, further including one or more shoulder straps that are coupled to the upper member, the lower member, or both.

7. The active exoskeletal spinal orthosis of claim 1, further including one or more leg members that are coupled to one of the upper and lower members, whereby the one or more leg members provide resting support of the orthosis on a support surface when in use.

8. A method of orthotic treatment, comprising the steps of:
    attaching an orthosis to a user at two spaced locations along portions of the user's torso;
    detecting a bending of the spine by the user that applies pressure to at least a part of the orthosis; and
    applying a corrective moment, a distraction force, or both to the user's spine that at least partially counteracts the detected bending of the spine by actuating one or more of a plurality of actuators that extend between an upper member of the orthosis located at a first one of the spaced locations and a lower member of the orthosis located at a second one of the spaced locations.

9. The method of claim 8 wherein the step of applying a corrective moment, a distraction force, or both is performed continuously throughout a range of motion.

10. The method of claim 8 wherein the step of detecting a bending of the spine includes measuring with sensors one or more of the following types of physical parameters: stress, strain, temperature, humidity, position, velocity, acceleration, orientation, or muscle activity.

11. The method of claim 8 further including the step of recording data concerning the operation of the orthosis and communicating the data externally from the orthosis.

12. The method of claim 11, further including the step of modifying the method of orthotic treatment remotely and communicating the modifications externally to the orthosis.

\* \* \* \* \*